United States Patent [19]

Drolet

[11] 4,127,111
[45] Nov. 28, 1978

[54] AUTOMATIC BLOOD SAMPLING SYSTEM AND METHOD

[76] Inventor: Roland A. Drolet, 1150 Toison d'Or, Les Saules, Quebec, Canada

[21] Appl. No.: 735,811

[22] Filed: Oct. 26, 1976

[51] Int. Cl.² .............................................. A61M 5/00
[52] U.S. Cl. .................................... 128/2 G; 422/44; 422/81; 422/98
[58] Field of Search ............... 128/2 G, 214 B, 214 E, 128/2 F; 23/230 B, 253 R; 73/425.4 R, 425.4 P; 356/39–42

[56] References Cited

U.S. PATENT DOCUMENTS

| | | | |
|---|---|---|---|
| 2,455,810 | 12/1948 | Ryan | 128/2 G |
| 3,756,234 | 9/1973 | Kopp | 128/214 R |
| 3,838,682 | 10/1974 | Clark et al. | 128/2 G |
| 3,908,653 | 9/1975 | Kettering | 128/214 R |
| 3,910,256 | 10/1975 | Clark et al. | 128/2G |
| 3,995,623 | 12/1976 | Blake et al. | 128/2.05 F |
| 4,014,328 | 3/1977 | Cluff et al. | 128/2 F X |
| 4,030,888 | 6/1977 | Yamamoto et al. | 23/230 B |

OTHER PUBLICATIONS

Drolet et al., "Automatic Blood Sampling System", Intnl. Conference on Biomedical Transducers, Paris, 11/7/75.

*Primary Examiner*—William E. Kamm
*Assistant Examiner*—Francis J. Jaworski

[57] ABSTRACT

An automatic blood sampling system and method which are characterized by preventing the transmission of electric shocks to the patient, by the use of only very small blood samples, by evacuating the used blood samples to waste and thus permitting the conduct of destructive tests on the samples, and by automatic and safe cleaning and rinsing of the tubing. This system distinctively defines a pair of mini-bypasses for the blood of a patient to produce blood circulation by-passing the blood stream of the patient and to withdraw the blood samples from the mini-bypasses, upon command from an automatic blood analyser and actuation by a logic circuit. The latter actuates the necessary electromagnetic valves by a binary coding corresponding to the "on" and "off" states respectively and to produce BLOOD SAMPLING, STANDBY, WASTE, WASH and FEED SAMPLE states of actuation of the valves in response to changes in the states of operation of the automatic blood analyser.

2 Claims, 8 Drawing Figures

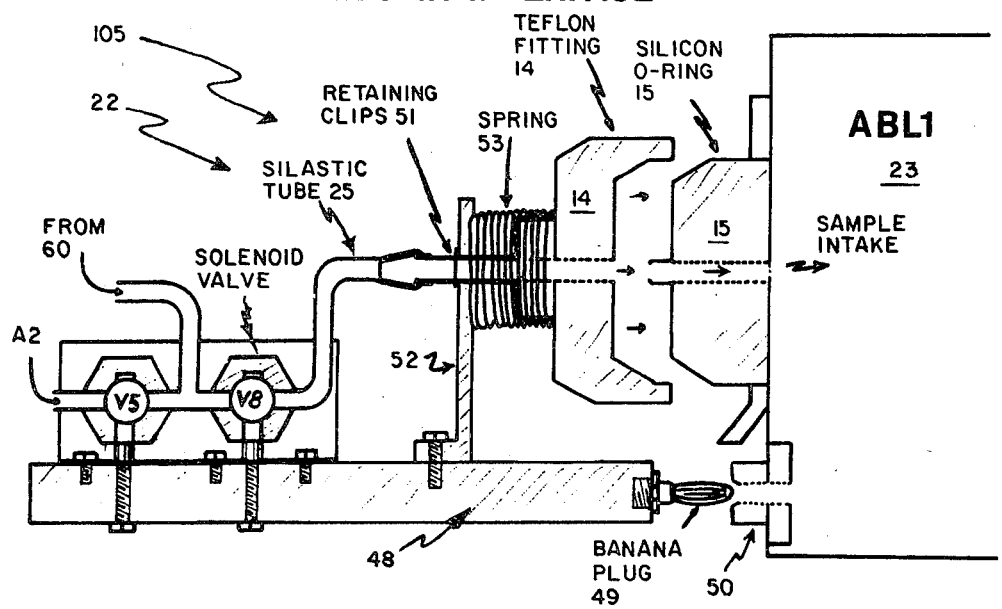
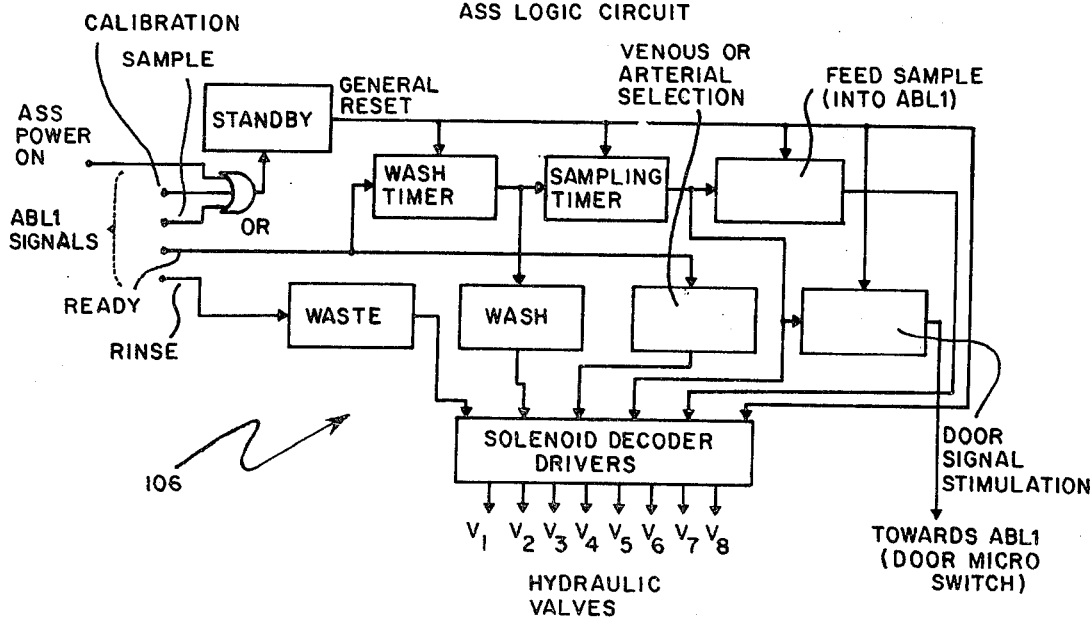

AUTOMATIC BLOOD SAMPLING SYSTEM AND METHOD

BACKGROUND

1. Field of invention

This invention relates to automated blood or liquid analysis systems and, more particularly, to an apparatus and method for automatically withdrawing and testing blood or other liquids.

2. Prior Art

As known for years, the treatment of patients who are critically ill with respiratory or cardiovascular disorders require frequent measurement of various blood parameters such as pH, $pO_2$, $pCO_2$, HB, $HCO_3$, $TCO_2$, BE, SBE, $SatO_2$, and SBC. While oxygenation is necessary for the maintenance of life, it is also important to reduce the duration of high oxygen concentration to a minimum in order to prevent possible toxic effects in the lungs. There are numerous other situations, such as in diagnosis of critical illness, patient monitoring during certain corrective procedures and intensive care programs wherein blood parameters must be frequently measured, analysed and controlled.

However, frequent manual withdrawal of blood is undesirable due to the increased opportunity for the entrance of air emboli in the blood stream. Similarly, multiple usage of an indwelling catheter requires re-arrangement of external tubing to adjust between blood withdrawal and irrigation configurations, which is subject to human error and which also presents increased incidence of air emboli infusion. Some systems known to the art return the analyzed blood to the patient after the measuring cycle, which procedure can create some possibility of patient contamination. On the other hand, systems known to the art which discharge withdrawn blood to waste after analysis thereof have utilized blood samples of an excessive volume. Other systems subject the patient to a risk of electric shock due to a continuous contact existing between the patient and electric potentials within the blood testing equipment or sensors. Also, systems which return blood to the patient cannot be used for destructive tests, such as glucose analyses, flame photometry etc...

Saline solution is commonly used as a compatible vehicle for use in blood pumps and tubing systems of blood test units, since some of its chemical properties approach that of blood. However, some blood parameters differ markedly from saline solution and pure water, which are used for cleaning a blood analysis system, and this may require a test principle which includes a slow process, such as diffusion across a membrane. Also, any repetitive usage of an accurate blood analysis system requires washout between samples. An efficient usage of such a system requires a rather rapid analysis cycle. Most blood analysis units known to the art require manual cleaning and/or manual calibrations between samples.

OBJECTS AND BRIEF SUMMARY OF THE INVENTION

A principal object of the invention is to provide improved blood analysis capability.

Another object of the invention is to provide improved automatic blood withdrawal and analysis apparatus and method.

A further object of the invention is to provide an automatic blood withdrawal and analysis system which reduces the possibility of patient contamination and which, at all times, isolates electrically the blood circulating in the patient from the blood gas analyser, thus eliminating the risk of electrical shock to the patient arising from the blood analysis system.

A further object of the invention is the provision of an automatic blood sampling system which is compatible with a known reliable blood gas analyser, and which can be adapted to different blood gas analysers known to the art.

A further object of the invention is the provision of an automatic blood sampling system capable of sampling blood at two different sites (such as arterial and venous sites) of the cardiovascular system and introduce the blood samples into a single blood gas analyser with an adjustable time interval between successive sampling.

Another object of the invention is to provide an automatic blood gas analysis system which analyses arterial and/or venous blood at adjustable time intervals using very small blood samples.

Another object of the invention is to provide an automatic blood sampling system capable of sampling blood from a continuous blood bypass circulation or from a double lumen indwelling catheter placed in an artery or in a vein.

A further object of the invention is to provide an automatic blood sampling and analysis system which is self-cleaning after every analysis cycle, and which can be used during long term cardiorespiratory assistance (which may last more than one week without interruption).

Another important object of the invention is to provide an analyser-withdrawal configuration where only the withdrawal unit requires sterilization, and where contamination of the withdrawal unit by the analyser is precluded.

A further object of the invention is to reduce to no more than five minutes the time necessary for obtaining complete results of blood gas analysis using an on-line intermittent blood gas analysis system.

A further object of the invention is to provide an automatic sampling system for gas analysis of other liquids than blood.

According to the present invention, an automatic blood sampling system is adapted for connection with a blood extracorporal circuit (or with double lumen indwelling catheters) and a commercial blood gas analyser. The present invention provides an automatic blood sampling system which is capable of sampling blood at two different sites (arterial and venous) of a blood extracorporal "bypass" circulation, and which introduces the blood samples into a blood gas analyser at adjustable time intervals.

The invention provides an automatic blood sampling system which is compatible with the analyser and which can be adapted to other blood gas analysers as they become available on the market.

The present invention provides a blood sampling and analysis system which can print out complete results of a blood gas analysis every five minutes using only 0.5 $cm^3$ of blood for measurements of pH, $pO_2$, $pCO_2$, and hemoglobin. Other parameters such as $HCO_3$, $TCO_2$, BE, SBE, SBC and oxygen saturation are calculated by a mini-computer incorporated in the said analyser and results of measured and calculated parameters are printed on paper by the said analyser.

The invention provides an automatic blood sampling system essentially composed of:
  an hydraulic circuit through which venous and arterial blood samples are taken;
  a special roller-pump for maintaining a continuous blood flow in a venous and an arterial mini-bypass;
  a logic circuit which controls eight hydraulic valves in a programmed fashion such as to allow the said roller-pump to withdraw blood samples from the said mini-bypass; to allow a pressurized air source to push the said blood samples into the said analysing and to allow automatic cleaning of the withdrawal circuit after each analyser cycle of the said analyser;
  a plug-in interface through which blood is fed into the said analyser.

The hydraulic circuit of the present invention is preferably made of "Silastic" sold by the Dow Corning Company. The hydraulic circuit has preferably an inner diameter of 1/16 inch and an outer diameter of ⅛ inch. The central part of this circuit is molded in a single piece, preferably using Dow Corning Liquid "Silastic", Type MDX-4-4210.

The logic circuit of the automatic sampling system (ASS) essentially controls the state transitions of the ASS. The ASS is automatically cleaned by the RINSE cycle of the analyser. The state READY of the analyser initiates cleaning of the automatic sampling system (ASS). When cleaning is completed, venous or arterial sampling occurs after which operation the ASS returns into a STANDBY state, waiting for a new READY initiating signal from the said analyser. A complete measurement and cleaning cycle last only five minutes, except when the analyser enters its calibration state which lasts 6 minutes. After the measuring and cleaning cycles, the ASS returns to its STANDBY state, and so on.

The present invention provides an automatic blood withdrawal and analysis system which reduces the possibility of patient contamination and which isolates (electrically), at all times, the blood circulating in the patient from the analyser, thus eliminating the risk of electrical shock to the patient arising from the analyser.

The ASS of the invention is tested ex-vivo (using Mongrel dogs) by connecting the said hydraulic circuit of the ASS to one femoral vein and one femoral artery of dog. The coagulation time, measured with an "Hemochron" (Type 400, from International Technidyne) is maintained within clinically acceptable range by proper administration of heparin. Also, 10 USP per $cm^3$ of heparin is added to the rinsing saline solution of the analyser, in order to prevent blood coagulation in the hydraulic circuit of the ASS during long term automatic operation. The invention provides an on-line automatic sampling system which, when connected to the analyser, gives values of blood parameters in agreement with independent measurements performed with known precision laboratory instruments.

Other objects, features and advantages of the present invention will become more apparent in light of the following detailed description of a preferred embodiment thereof, as illustrated in the accompanying drawings, in which:

BRIEF DESCRIPTION OF THE DRAWINGS

FIG. 4 is a drawing of the ASS-ABL1 "plug-in interface", not to scale;

FIG. 5 is a block diagram of the ASS logic circuit;

DESCRIPTION OF A PREFERRED EMBODIMENT

Figure 1:
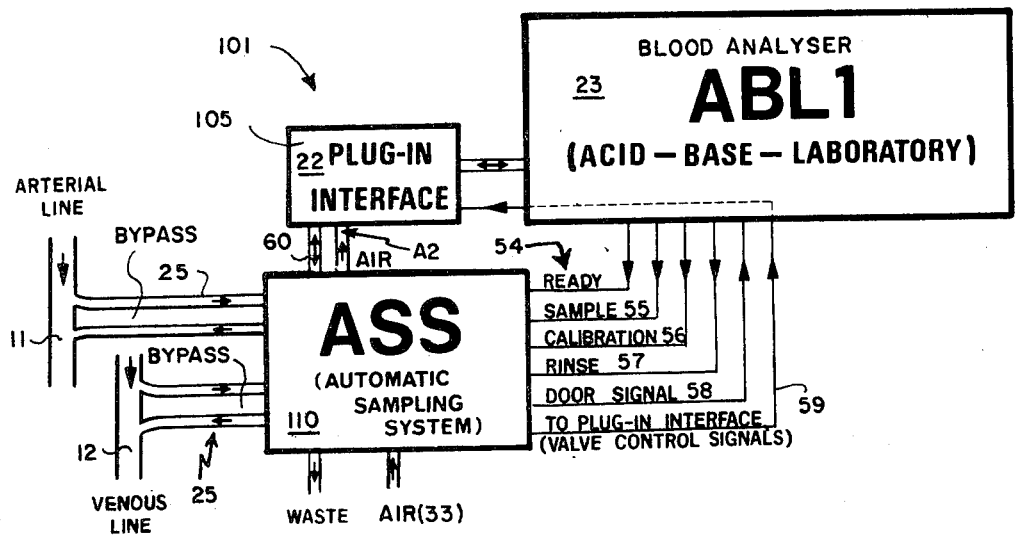
FIG. 1 shows a diagram of the complete system including the automatic blood sampling system, the blood gas analyser and the plug-in interface.

Referring now to FIG. 1, a blood analysis system 101 which may incorporate the precepts of the present invention includes a blood gas analyser 23 (or its equivalent); an automatic sampling system 110 composed essentially of a hydraulic circuit and a logic circuit; a plug-in interface through which the said ASS 110 introduces blood samples into the analyser 23, a venous bypass 12, 11 and/or an arterial bypass 13, 11; an adjustable air source 33, 32, 34, 35, 36 serving to push blood samples through the plug-in interface 22 and into the blood analyser 23. The logic circuit 42 of the ASS, 110 communicates with the analyser 23, using different control signals 54, 55, 56, 57, and 58. The hydraulic valves of the plug-in interface 22 are controlled by the ASS, 110, via the analyser 23, 59. It should be understood that the blood gas analyser 23 is not germane to the present invention; instead, the present invention is concerned with the improvements in an automatic sampling system 110 and in the interconnections of this sampling system 110 with the gas analyser 23 and the blood circulation 12, 13 of the patient, as described with respect to FIG. 2, FIG. 3, FIG. 4, FIG. 5, Table 1, FIG. 6, and FIG. 7 hereinafter, and the timing of functions performed thereby, so as to achieve new and improved operational functions and results.

Figure 2:
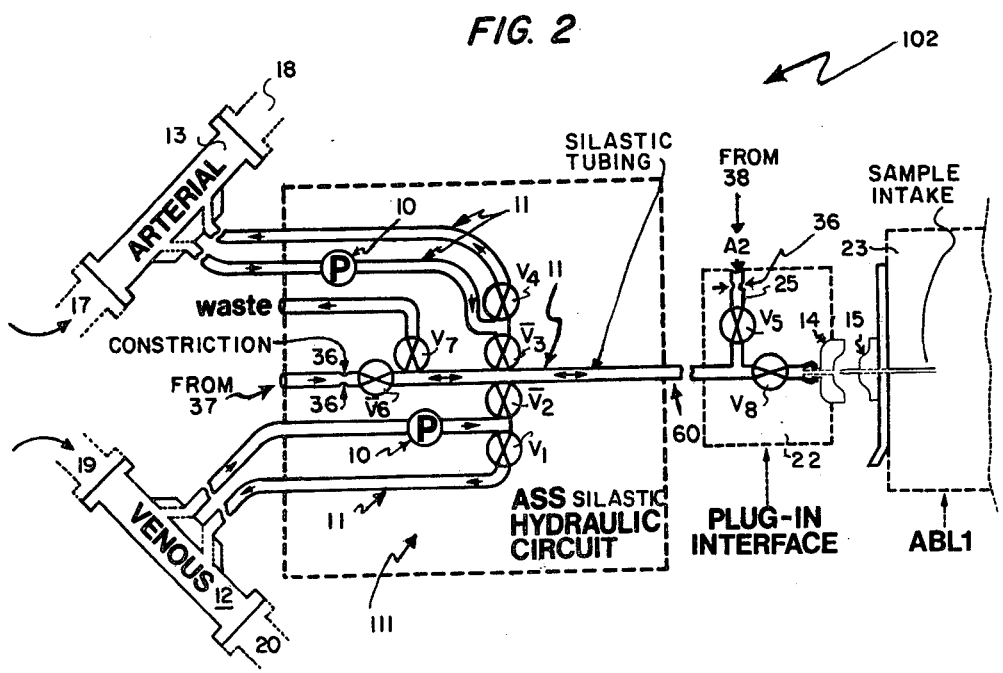
FIG. 2 is a schematic representation of the automatic sampling system connected to venous and arterial lines and to the blood gas analyser.

Referring now to FIG. 2, which is a schematic representation of the hydraulic circuit 111 of the automatic blood sampling system 110 and its inter-connections with the venous and arterial lines 12, 13 and with the blood analyser 23. This diagram is not drawn to scale. The size as well as the detailed description of the elements shown in this diagram is described in greater details with respect to FIG. 3 hereinafter. Blood withdrawn from the arterial line 17, 18 is continuously circulated through an arterial mini-bypass 13, 11 with the special roller-pump 10 (this pump is described with respect to FIG. 3 hereinafter) and reinjected into the same line 17, 18. Similarly, blood withdrawn from the venous line 19, 20 is continuously circulated through a venous mini-bypass 12, 11 with the said roller-pump 10, and reinjected into the same line 19, 20. The continuous circulation of blood in the mini-bypass prevents the stagnation of blood in this part of the blood sampling system. The connectors 12, 13 and the tubing circuit 11 may be molded in "Silastic" or in another equivalent biocompatible material. The Silastic tube 11 has an inner diameter of 1/16 inch and an outer diameter of ⅛ inch and is commercially available. The central part of the tubing circuit 11 (where the Solenoid valves V1, V2, V3, V4, V6, V7 are adapted) is molded using Dow Corning liquid Silastic, Type MDX-4-4210, or its equivalent. The connectors 12, 13 have an inner diameter of ⅜ inch and an outer diameter of 9/16 inch and may be of different sizes for other applications. Each connector 12 or 13 may be replaced by a modified double lumen indwelling catheter of a well known type. The said catheter is modified so as to have its two lumen at a distance of at least ½ inch. The size of the "Silastic" tubing 11 is chosen according to the size of the said catheter. The plug-in interface 22 is composed of two valves V5 and V8 and a "Silastic" tubing 25 of the type described above, and a spring-loaded "Teflon" fitting 14. This interface 22 is described with respect to FIG. 4 hereinafter. The valves V1, V2, V3, V4, V5, V6, V7, and V8 are electromagnetic valves of a known type operated by an electric current. As a bleeding safety measure, and also for prevention of air emboli in cases of a power failure during operation of the said sampling system, the said valves V2, V3, and V6 remain closed when their corresponding solenoids K2, K3, and K6 are not excited electrically. The solenoids K1, K4, K5, K7, and K8 are excited with 12 Volts as described with respect to FIG. 7 hereinafter. The constriction 36 represents an air flow adjustment which uses a small screw 36 as a variable constriction as described with respect to FIG. 3 hereinafter.

The central part of the "Silastic" tubing 103 of the ASS hydraulic circuit 111 is composed of "Silastic" Tubes 25 (P.D. = ⅛ inch; I.D. = 1/16 inch) commercially available which are fixed together by means of molded joints 24 to the central molded part 11 of the hydraulic circuit 111. The said central part 11 is molded with Dow Corning Liquid Silastic of Type MDX-4-4210, or with its equivalent. All molded joints are molded with the said liquid Silastic 24 (Dow Corning, Type MDX-4-4210) or with its equivalent.

Figure 3:
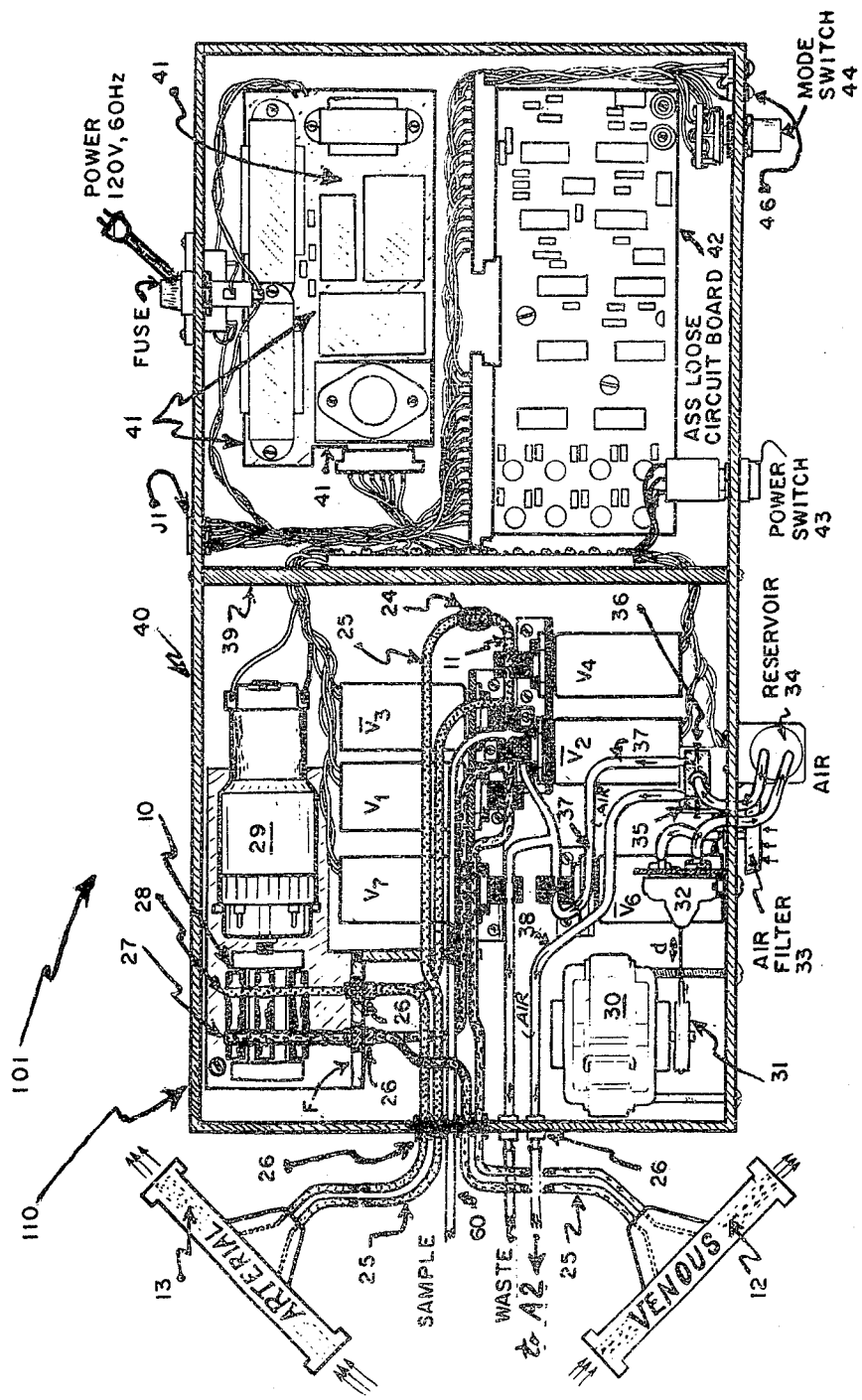
FIG. 3 is a detailed drawing of the automatic sampling system (see the one-inch scale at the lower right corner of the drawing). The hydraulic circuit is shown on the left-hand side of the drawing. The power supply and the logic circuit board are shown on the right-hand side of this drawing.

Referring now to FIG. 3, which is relatively complete scale drawing of the automatic sampling system 110. The one-inch scale is shown in the lower right-hand corner. This sytem 104 includes arterial and venous connectors 12, 13 and an hydraulic circuit 11, 24, 25, 26, 27, and 28. Teflon connectors 26 are used for interconnecting "Silastic" tubing 25. A roller-pump 10, activated by a six-speed motor 29 of a known type (6 volts, 0.14 A to 1.1A), maintains continuous blood flow in an arterial mini-bypass 13, 25, 28 and in a venous mini-bypass 12, 25, 27. The "Silastic" tubes 27 and 28 have specific sizes and lengths so as to allow the non-occlusive roller-pump 10 to maintain equal blood flow rates in the two mini-bypass (arterial and venous). The sizes and lengths of these two Silastic tubes are the following:

for the arterial "pumping" tube 28, length = 3 ⅛ inches, I.D. = 1/16 inch, O.D. = 3/32 inch; and for the venous "pumping" tube 27, length = 3 ¼ inches I.D. = 3/32 inch, and O.D. = ⅛ inch. The distance from the axle of the roller-pump 10 to the fixation plane F, the length and diameter of the four rollers (only three are seen in FIG. 3) of the rollerpump 10 can all be measured on the present drawing 104 by using the 1 inch scale shown in the lower right-hand corner of this drawing. The vertical distance between the lower and upper Teflon connectors 26 of the venous tube 27 is ½ inch (note that only the upper connector 26 is seen here). Each end of the arterial tube 28 is fixed to a Teflon connector of Type 26 in a manner similar to that just described for the venous tube 27. The two Teflon connectors to which the tube 28 is fixed have an inner diameter of 1/16 inch. $V_7$, $V_1$, $V_3$, $V_4$, $V_2$, and $V_6$ are solenoid valves as described with respect to FIG. 2 hereinbefore and Table 1 hereinafter. With the connector 12 used for blood withdrawal, there is practically no possibility of air bubble suction near the connector, since the tubing 25 is molded with the connector 12. Also, air suction into the venous mini-bypass 12, 25, 26, 27 or into the arterial mini-bypass may be prevented by replacing the Teflon connectors 26 by molded liquid Silastic joints 24. However, for maximum safety, an automatic air detector of a known type, not shown in 104, is located in a region of the tubing 25 where the hydraulic blood pressure may become negative with respect to atmospheric pressure, and the air detector automatically switches the motor 29 off. Therefore, if in any possible circumstances, air is present in the mini-bypass, the pump 10 stops and air bubbles may be pushed out of the venous or arterial mini-bypass using the well known procedure for air elimination from a blood circuit. This procedure consists in pushing air bubbles out through a three-way valve arrangement (not shown in FIG. 3 at 104) previously incorporated in the blood circuit: the roller-pump 10 is slowly activated while the three-way valve arrangement allows the expulsion of air bubbles from the blood circuit into the atmosphere. This three-way valve arrangement includes a T-shaped Silastic tubing incorporated in the blood return path of the mini-bypass by means of molded joints of Type 24; one hydraulic valve used to allow the air to be pushed out of the mini-bypass; and a second valve placed on the blood return path (after the T-shaped Silastic junction). The latter valve is mechanically linked to the air outlet valve so that when this outlet valve is open, the second valve automatically closes and inversely. This safety feature prevents any air from entering into the blood circulation of the patient. When all air is eliminated from the blood circuit, the motor 29 is allowed to activate the pump 10, and so on. An air source 33, 32, 34, 35, 36, and 37 pushes the blood samples into the analyser 23 when so ordered by the logic circuit 42 of the sampling system. This air source is composed of an air filter 33, a diaphragm pump 32 activated by a motor 30 generating a displacement "d" of 1/16 inch, a 10 cm$^3$ air reservoir 34 for preventing any fluid from damaging the pump 32, and an air divider 35 with two small screws 36 for adjusting the flow rate of air in the two tubing circuit 37 and 38. Also shown in FIG. 3 at 104, is the physical location of components of the logic circuit 42 and of the DC power supply 41. This power supply 41 serves for operating the logic circuit 42, the two motors 29 and 30 and the solenoid valves $V_1$, $V_2$, $V_3$, $V_4$, $V_5$, $V_6$, $V_7$, and $V_8$. The detailed electronic circuits of the power supply 41 and of the logic circuit 42 are described with respect to FIG. 6 hereinafter. The front panel of the apparatus 110 also contains the main power switch 43 and the mode switch 44 used to select the mode of operation of the system. This mode switch 44 has four positions: OFF, VA, V and A. When the switch 44 is in the VA position, the sampling system 110 takes venous and arterial blood samples alternately; when this switch 44 is in the "V" position, the sampling system takes only venous blood samples and when the same switch 44 is in the "A" position, the sampling system takes only arterial blood samples. In all cases, the indicator light 45 is ON when arterial blood is being analysed and the indicator light 46 is ON when venous blood is being analysed. The rear of the apparatus 110 contains a 1.0 Amp. fuse and the connector Ji (for 10 connections) to which a cable extension for interconnecting the sampling system 110 to the blood gas analyser 23 (see also FIG. 6 hereinafter).

Referring now to FIG. 4, a "plug-in" interface 105 serves as interconnection between the ASS, 110, and the analyser 23. This interface 105 includes Silastic tubing 25 (I.D. = 1/16 inch; O.D. = ⅛ inch) in which blood samples are pushed, 60, towards the blood sample intake 15 of the analyser 23. The valves $V_5$ and $V_8$ control the flow of blood, saline, gas or air according to a "Valve State Code" as described with respect to Table 1, FIG. 5, FIG. 6, and FIG. 7 hereinafter. The interface 105 is plugged to the sample intake O-ring 15 and into two banana plug 49 female connectors 50. A vertical support 52, fixed to the base 48 of the "plug-in" 105, presses a spring-loaded 53 Teflon fitting 14 which insures the water-tightness of the connection 14, 15. A retaining clip 51 keeps the fitting 14 attached to the support 52 when the "plug-in" 105 is taken away from the analyser 23. The air source 33, 32, 34, and 35 is connected to the "plug-in" via the Silastic tube A2, as described with respect to FIG. 3 hereinbefore.

simulated "Door signal" which is a logic signal given by the ASS, 110, to the analyser 23:

"Door signal" = 0, (when the analyser 23 "sees" its intake door as closed);

"Door signal" = 1, (when the said analyser "sees" its intake door as open);

ASS state-transition signal: for example, three of the six so-called ASS states are generated by different control signals of the analyser 23. More specifically, the control signals termed SAMPLE and CALIBRATION generate the STANDBY state of the said ASS; the control signal RINSE generates the WASTE state of the said ASS and the control signal READY generates the WASH state of the said ASS. A complete description of the state transitions of the said ADD is provided with respect fo FIG. 7 hereinafter;

"bleeding safety feature": as seen from Table 1, the hydraulic valves $V_2$, $V_3$, and $V_6$ remain closed when their corresponding solenoids $K_2$, $K_3$, and $K_6$ are not excited electrically. This feature prevents bleeding of the patient through the said ASS when the power supply of the said ASS fails or when it is turned OFF accidentally by the user. The TRUTH-TABLE described herein is the basis for designing the logic circuit 42 of the said ASS. The said logic circuit is described with respect to FIG. 5 and FIG. 6 hereinafter.

Referring now to FIG. 5, different control signals (CALIBRATION, SAMPLE, READY and RINSE)

TABLE 1.

"TRUTH-TABLE" or "VALVE STATE CODE" for the "Automatic Blood Sampling System".

| | Corresponding ASS output signals | | | |
|---|---|---|---|---|
| | 0 = valve closed | | 0 = not excited (solenoid) | |
| ASS states | HYDRAULIC VALVE STATES | | SOLENOID STATES | "DOOR" of ABL1 |
| | $V_1$ $V_2$ $V_3$ $V_4$ $V_5$ $V_6$ $V_7$ $V_8$ | | $K_1$ $K_2$ $K_3$ $K_4$ $K_5$ $K_6$ $K_7$ | $K_8$ |
| STANDBY | 1 0 0 1 1 0 1 1 | | 0 0 0 0 0 0 0 | 0 |
| WASTE | 1 0 0 1 0 0 1 1 | | 0 0 0 0 1 0 0 | 0 |
| WASH | 1 0 0 1 1 0 1 0 | | 0 0 0 0 0 0 1 | 0 |
| VENUS sampling | 0 1 0 1 0 0 0 1 | | 1 1 0 0 1 0 1 | 1 |
| ARTERIAL sampling | 1 0 1 0 0 0 0 1 | | 0 0 1 1 1 0 1 | 1 |
| FEED SAMPLE | 1 0 0 1 0 1 0 1 | | 0 0 0 0 1 1 1 | 1 |

0 = Valve Close
0 = relay not energized

Referring now to Table 1 on the next page, which is named the "Truth-Table" or "Valve-State Code" of the blood analyis system 101, the state of hydraulic valves $V_1$, $V_2$, $V_3$, $V_4$, $V_5$, $V_6$, $V_7$, $V_8$ and the state of their corresponding solenoids $K_1$, $K_2$, $K_3$, $K_4$, $K_5$, $K_6$, $K_7$, and $K_8$ are indicated for each ASS state STANDBY, WASTE, WASH, VENOUS SAMPLING, ARTERIAL SAMPLING and FEED SAMPLE which states are defined thereby. In fact, the said ASS states are completely defined by the position (open or closed) of the eight hydraulic valves, the state of the corresponding eight solenoids, and the simulated "DOOR" signal generated by the ASS logic circuit 42. In order to provide a clear understanding of the said TRUTH-TABLE, a few important terms are now explained:

$V_1$, $V_2$ ... or $V_8$ = 0, (when the valve is physically closed);
and
$V_1$, $V_2$ ... or $V_8$ = 1, (when the valve is open);
solenoids: each hydraulic valve is controlled by a solenoid;
solenoid states:

$K_1$, $K_2$, ... or $K_8$ = 1, (when excited electrically);
and
$K_1$, $K_2$, ... or $K_8$ = 0, (when not excited electrically);

of the analyser 23 generate the said ASS states (STANDBY, WASTE, WASH, VENOUS or ARTERIAL SAMPLING and FEED SAMPLE). The door signal is simulated by the logic circuit 42. This logic circuit activates the eight solenoids of the eight hydraulic valves according to the said TRUTH-TABLE (TABLE 1) and more generally, according to the organigram 108 of the complete analysis system 101. The detailed circuit drawing of the logic circuit is described with respect to FIG. 6 hereinafter.

Figure 6:
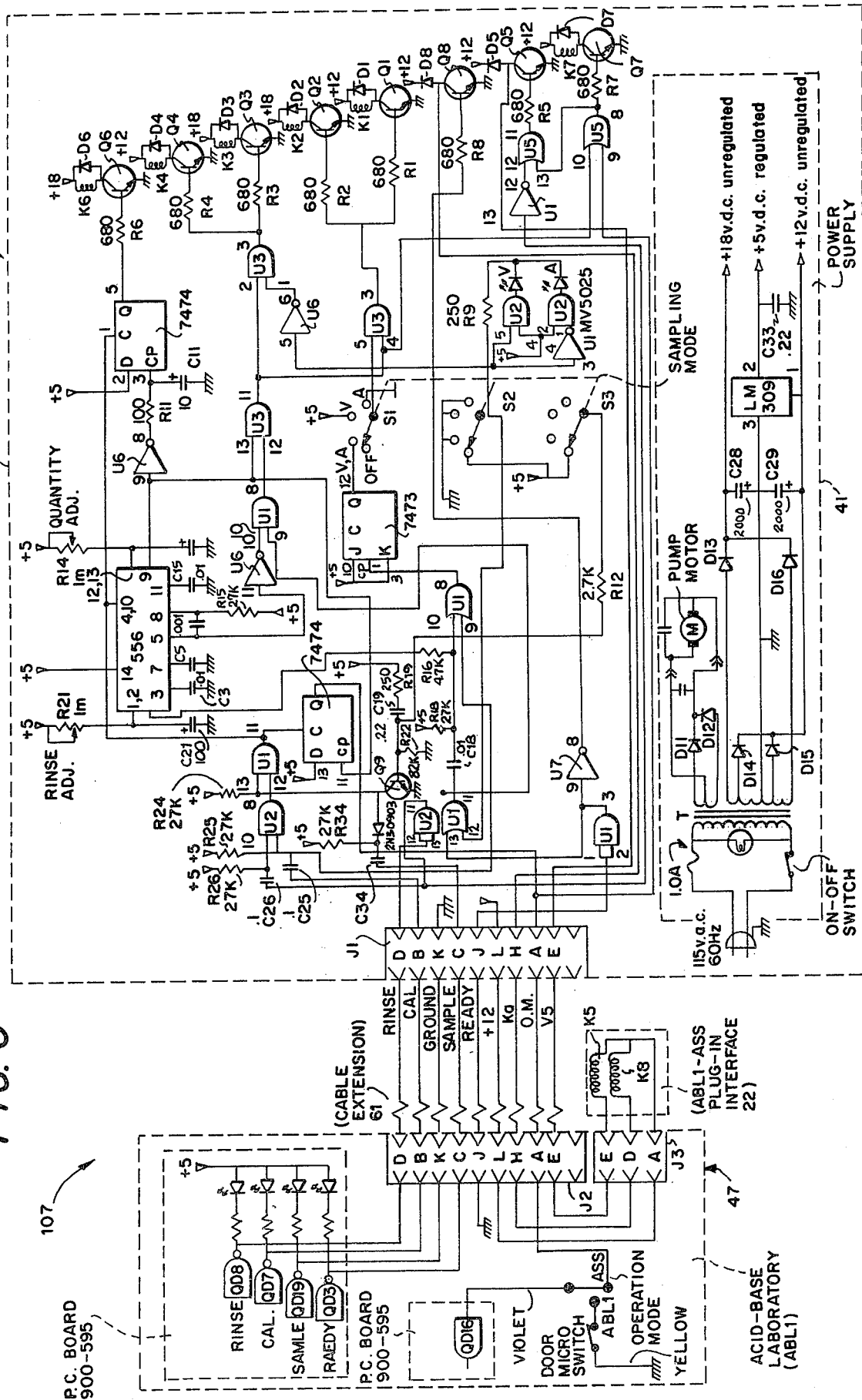
FIG. 6 shows the complete logic circuit of the ASS. Details of the connection of the ASS to the ABL1 are shown on the left-hand side and the circuit of the ASS power supply is shown in the lower half of this diagram.

Referring now to FIG. 6, the detailed circuit 107 of the analysis system 101 (excluding the electronic circuits of the analyser 23) includes the complete electronic circuit diagram of the logic circuit 42, the circuit diagram 47 of minor modifications of the gas analyser 23 (ABL1 from Radiometer Company) the circuit diagram of the "plug-in interface 22, and the detailed circuit diagram 41 of the power supply 41 providing DC power (5 volts, 12 volts and 18 volts) for the logic circuit 42. The circuit diagram of the power supply for the roller-pump motor 29 (shown as "M" in this drawing 41) is incorporated to the power supply circuit 41. The 5 volt DC power supply taken from the circuit 41 is regulated, and 12-volt and 18-volt power supplies taken from the circuit 41 are not regulated. The circuit 107 shows the cable extension 61 which connects the logic circuit 42 and the power supply 41 to the analyser interface 47, the multi-wire connectors J1, J2 and J3 which are connected to the cable extension 61 and to the "plug-in" interface 22. The interface 47 also shows connection of the logic circuit 42 to the control unit 5 (P.C. board No: 900-595) of the analyser 23 including the RINSE, CALIBRATION, SAMPLE and READY control signals from the analyser 23; and the operation-mode switch of the analyser 23 which switch allows for using the analyser 23 associated with the ASS, 110, or without the ASS by removing the plug-in interface 22 and introducing blood samples manually into the sample inlet 15 of the analyser 23. The circuit 107 also shows the solenoids $K_1$, $K_2$, $K_3$, $K_4$, $K_5$, $K_6$, $K_7$, and $K_8$ of the hydraulic valves $V_1$, $V_2$ ... $V_8$; the integrated circuits 556, 7473 and 7474. A legend for the circuit elements of circuit 107 is shown on the lower right-hand corner of this circuit 107. All other symbols like $R_1$, $R_2$ ... $R_{34}$; $C_1$, $C_2$, ... $C_{33}$, $Q_1$, $Q_2$, ... $Q_8$; $D_1$, $D_2$, ... $D_{16}$; U1, U2, U3, and U4 are standard symbols accepted by international associations of electrical and electronic engineers, like the IEEE for example. The complete electronic circuit 107 operates the hydraulic valves $V_1$, $V_2$, $V_3$, $V_4$, $V_5$, $V_6$, $V_7$, $V_8$ according to the TRUTH-TABLE of the said ASS as described with respect to TABLE 1, and more generally, according to the organigram 108 of the analysis system 101 as described with respect to FIG. 7 hereinafter.

Figure 7:
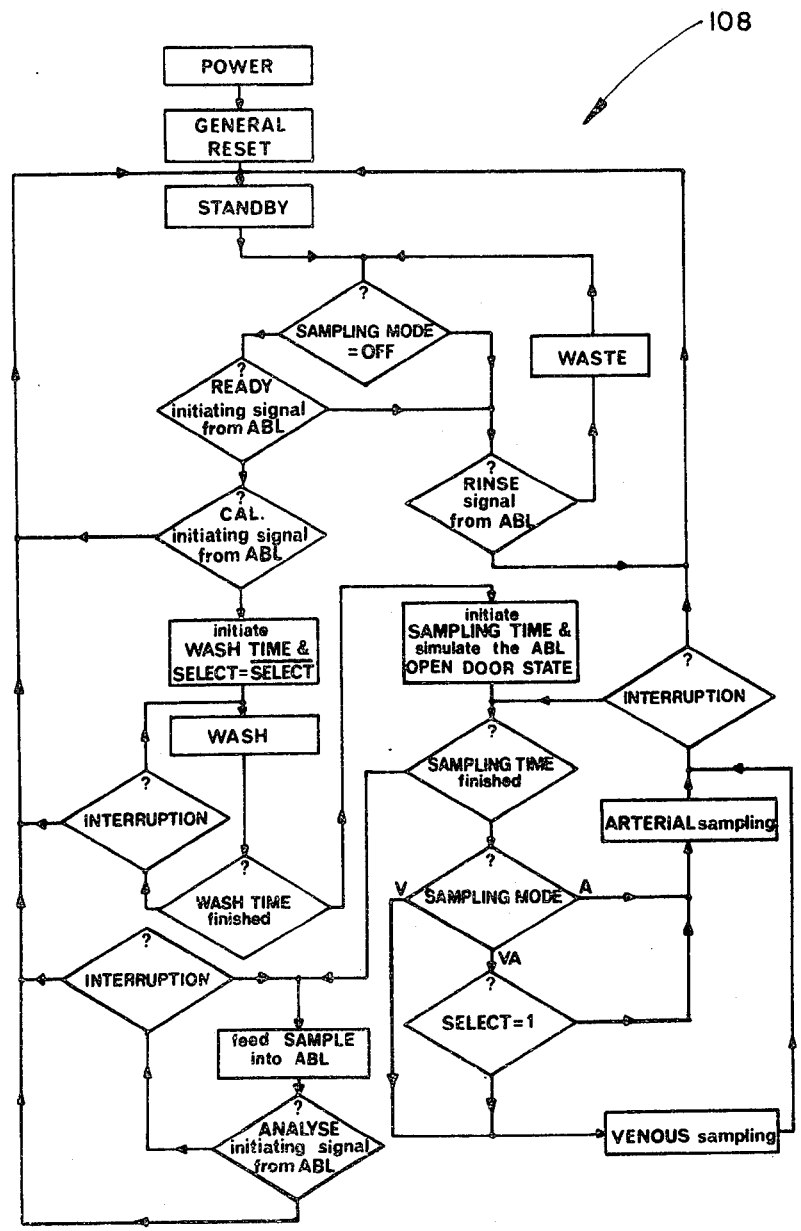
FIG. 7 shows the organigram of the ASS. This diagram illustrates the logical operations of the ASS.

Referring now to FIG. 7, which is an organigram 108 of the analysis system 101, when the power supply 41 is switched on 43, the ASS goes into its STANDBY state defined in TABLE 1. If the sampling mode switch 44 is not in the OFF position, the logic circuit 42 checks if there is a READY initiating signal from the analyser 23 (ABL1). If the answer to the last question is NO, then the logic circuit 42 checks if there is a RINSE signal from the analyser 23 (ABL1); if NO, the ASS goes into its STANDBY state, and if YES the ASS goes into its WASTE state (defined in TABLE 1) as described with respect to FIG. 5 hereinbefore. When there is a READY initiating signal from the analyser 23, the logic circuit 42 of the ASS checks if there is a CALIBRATION initiating signal from the analyser 23; if the answer is YES, the ASS returns into its STANDBY state; and if the answer is NO, the logic circuit 42 initiates a WASH timer and selects either venous sampling or arterial sampling in an alternating way (the logic variable termed SELECT takes the values 0 and 1 alternately, corresponding to the VENOUS and ARTERIAL sampling states defined in TABLE 1 hereinbefore). Then the ASS goes into its WASH states defined in TABLE 1, unless an INTERRUPTION occurs from a manually-ordered RINSE signal (by ordering a RINSE from the analyser 23), or from a CALIBRATION signal generated by the analyser 23. When the WASH time is over, the logic circuit 42 initiates a SAMPLING timer and simulates an "OPEN DOOR" state of the analyser 23. Then the logic circuit 42 checks if the SAMPLING time is finished; if NO, depending on the position of the sampling-mode-switch 44 (which has four positions: OFF, VA, V and A as described with respect to FIG. 4 hereinbefore), the ASS goes into its ARTERIAL or VENOUS sampling states, which states are defined in TABLE 1 hereinbefore, and when the SAMPLING TIME is finished, the ASS enters into its "FEED SAMPLE" state, which state is defined in the TABLE 1. When the analyser 23 has received enough blood, a light-emitting diode, of a known type, initiates the ANALYSE cycle of the analyser 23. During this ANALYSE cycle, the analyser 23 sends a logic control signal termed SAMPLE to the logic circuit 42. If there is an INTERRUPTION of the type described with respect to the present FIGURE, the ASS immediately returns into its STANDBY state; and if there is no INTERRUPTION, the ASS returns into its STANDBY state only when the analyser 23 has received enough blood for gas analysis.

Figure 8:
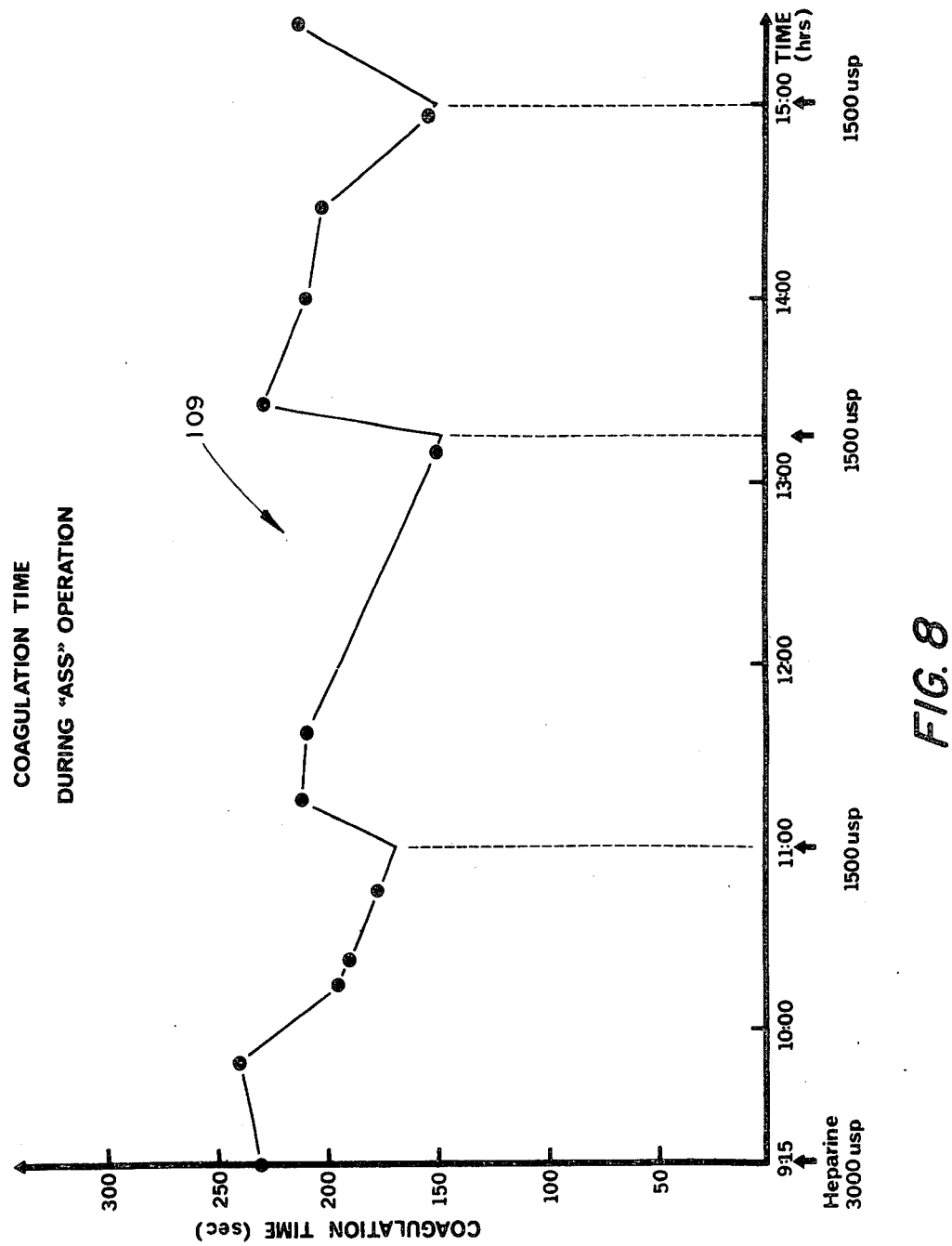
FIG. 8 is a graph showing the results of a canine experiment indicating values of the blood coagulation time during ASS operation.

The embodiment of the invention described hereinbefore thus provides a compact and very compatible blood sampling system which, according to the invention, may withdraw venous and/or arterial blood directly from a vein and/or an artery of a patient through a double lumen indwelling catheter or from a venous and/or arterial lines of an extracorporal blood circulation, and automatically introduces the withdrawn blood sample into a known blood gas analyser. With the said sampling system, there is practically no risk of air injection into the patient. The risk of electrical shock to the patient is also practically eliminated, since there is no low-electrical-resistance path between the blood gas analyser and the patient. In addition, the described embodiment provides automatic cleaning of the withdrawal tubing using the automatic RINSE cycle of a known blood gas analyser. The analyser uses saline solution and $CO_2$ alternately during its RINSE cycle, in order to provide for pre-establishment of a certain level of carbonate in the gas detector, which feature reduces the time necessary for equilibrium thereof. The described sampling system is tested ex-vivo, using Mongrel dogs, by connecting the hydraulic circuit of the sampling system to one femoral vein and one femoral artery of the animal. The coagulation time, measured with a known apparatus (the Hemochrom, Type 400, from International Technidyne Company), is maintained within clinically acceptable range (150 to 250 seconds) by proper administration of heparin to the animal. Also, heparin, 10 USP per $cm^3$ is added to the rinsing saline solution of the said analyser, in order to prevent blood coagulation in the hydraulic circuit of the sampling system during long term automatic operation. Referring to FIG. 8, the coagulation time is plotted 109 as a function of time, and doses of heparin given to the animal are indicated by arrows (3000 USP, etc. ...). In addition, the blood parameters measured on line with the described analysis system are in agreement with independent measurements of the same parameters using known precision laboratory instruments.

Although the invention has been shown and described with respect to a preferred embodiment thereof, it should be understood by those skilled in the art that various changes and omissions in the form and detail thereof may be made therein without departing from the spirit and the scope of the invention.

What I claim is:

1. A system for automatic sampling of blood and for the automatic feeding of a measured volume of blood to an automatic blood analyser, comprising a tubing having means at both ends for communicating said tubing with two spaced points of a blood vessel of a patient to establish a partial bypass, a power-operated pump means to continuously circulate blood at a constant rate of flow through said tubing by extracting blood from and returning it to said blood vessel, a blood sample withdrawal tubing adapted to be connected at one end to said analyzer, a compressed fluid source connected to the other end of said withdrawal tubing, a branch line tubing interconnecting intermediate points of said partial bypass tubing and of said withdrawal tubing, a first electromagnetic valve in said branch line tubing, a second electromagnetic valve in said withdrawal tubing serially mounted intermediate said fluid source and said branch line, and an electric command circuit means electrically connected to said two valves and giving timed commands to said valves causing opening of said first valve for a predetermined time to allow discharge of a predetermined volume of blood through said branch line within said withdrawal tubing, while said second valve is closed, then causing closing of said first valve and subsequent opening of said second valve, whereby said fluid under pressure pushes into said analyzer the measured quantity of blood in said withdrawal tubing.

2. A system as claimed in claim 1, further including a second branch line opening to waste and connected to said withdrawal tubing intermediate said first branch line and said other end of said withdrawal tubing, and a third electromagnetic valve in said second branch line, said electric command circuit means also electrically connected to said third valve and giving timed command to said third valve to cause the same to be in closed position when either one of said first and second valves are open and to cause opening of said third valve when both said first and second valves are closed, to thus allow the analyzer to clean the withdrawal tubing and to evacuate the content of the same through said second branch line to waste.

* * * * *